United States Patent
Rausch et al.

(10) Patent No.: US 8,079,752 B2
(45) Date of Patent: Dec. 20, 2011

(54) PROCESS AND MIXING UNIT FOR THE PREPARATION OF ISOCYANATES BY PHOSGENATION OF PRIMARY AMINES

(75) Inventors: Andreas Rausch, Neuss (DE); Christian Steffens, Köln (DE); Dietmar Wastian, Dormagen (DE); Manfred Keller-Killewald, Dormagen (DE); Matthias Böhm, Leverkusen (DE); Joachim Ritter, Leverkusen (DE); Marcus Grünewald, Dortmund (DE)

(73) Assignee: Bayer MaterialScience AG, Leverkusen (DE)

( * ) Notice: Subject to any disclaimer, the term of this patent is extended or adjusted under 35 U.S.C. 154(b) by 580 days.

(21) Appl. No.: 12/316,716

(22) Filed: Dec. 16, 2008

(65) Prior Publication Data
US 2009/0175121 A1    Jul. 9, 2009

(30) Foreign Application Priority Data
Dec. 19, 2007    (DE) .......................... 10 2007 061 688

(51) Int. Cl.
*B01F 7/10*    (2006.01)
(52) U.S. Cl. .................. 366/178.2; 366/181.4; 366/304; 422/225
(58) Field of Classification Search ............... 366/178.2, 366/178.3, 181.4, 304; 422/225
See application file for complete search history.

(56) References Cited

U.S. PATENT DOCUMENTS

| | | | |
|---|---|---|---|
| 4,086,663 A * | 4/1978 | Croft | .......................... 366/137.1 |
| 4,851,571 A | 7/1989 | Sauer et al. | |
| 4,886,368 A | 12/1989 | King | |
| 4,915,509 A | 4/1990 | Sauer et al. | |
| 5,117,048 A | 5/1992 | Zaby et al. | |
| 5,931,579 A | 8/1999 | Gallus et al. | |
| 6,896,401 B2 | 5/2005 | Wolfert et al. | |
| 2002/0067656 A1 | 6/2002 | Schuchardt | |
| 2006/0025556 A1 | 2/2006 | Koch et al. | |
| 2006/0252960 A1 | 11/2006 | Sohn et al. | |
| 2008/0200721 A1 | 8/2008 | Muller et al. | |

FOREIGN PATENT DOCUMENTS

| | | |
|---|---|---|
| DE | 4220239 C2 | 3/1960 |
| WO | 9833584 | 8/1998 |

OTHER PUBLICATIONS

J. Warnatz, U. Maas, R.W. Dibble, Combustion, Springer Verlag, Berlin Heidelberg New York, 2006, 4th edition, pp. 136-137.

\* cited by examiner

*Primary Examiner* — David Sorkin
(74) *Attorney, Agent, or Firm* — N. Denise Brown; Noland J. Cheung

(57) ABSTRACT

The invention relates to a mixer reactor of the rotor-stator type. This mixer reactor comprises a substantially rotationally symmetric housing which has a distributing chamber, a mixing chamber, a front plate that modifies the cross-section of the housing between these two chambers, and there are separate inlets into the mixing chamber for at least two substances and an outlet for removing the mixed material or product. The inlet for the first substance is provided in the axis of rotation of the mixing chamber. Two or more channels are aligned radially outward from this inlet, and the first substance is transported through these channels and into the mixing chamber. The inlet for the at least second substance is constructed in the form of a plurality of openings in the front plate, these inlet openings being are arranged rotationally symmetrically to the axis of rotation. Each of these inlet openings for the at least second substance has a corresponding pin which can be displaced in the axial direction.

16 Claims, 2 Drawing Sheets

PROCESS AND MIXING UNIT FOR THE PREPARATION OF ISOCYANATES BY PHOSGENATION OF PRIMARY AMINES

CROSS-REFERENCE TO RELATED PATENT APPLICATION

The present patent application claims the right of priority under 35 U.S.C. §119 (a)-(d) of German Patent Application No. 10 2007 061 688.2 filed Dec. 19, 2007.

BACKGROUND OF THE INVENTION

The invention relates to a process for the preparation of isocyanates by phosgenation of primary amines and to a mixing unit of the rotor-stator type which is suitable for mixing two or more different substances, including the educts phosgene and primary amine. The mixing unit of the rotor-stator type is a mixer reactor and is suitable for mixing, initiating and carrying out a reaction of at least two flowable substances which can have considerable differences in viscosity. This mixer reactor is particularly suitable for the preparation of mono- or polyisocyanates by reacting mono- or polyamines with phosgene dissolved in an organic solvent.

Rotor-stator mixers in general comprise at least one rotor provided with mixing elements and a stator surrounding the rotor which is equipped with elements which break the flow. Such rotor-stator mixers are generally known. In this context, the rotor rotates at a high speed of rotation, while the stator remains in a fixed position. By the movement of the rotor, the liquid in the annular gap between the rotor and the stator is mixed with high turbulence. In the case of non-miscible liquids, one of the two liquid is finely dispersed in the other by the high energy input. In this context, the dispersion formed is more finely dispersed as the speed of rotation increases (i.e. is higher), and therefore, the energy input is higher. Due to the high speed of rotation of the rotor, a large amount of energy is introduced into the liquid and converted into heat during the mixing. As a result, an increase in the temperature of the liquid mixture occurs in the course of the mixing operation.

It is known to carry out reactions which start rapidly, such as the preparation of mono- or polyisocyanates by reaction of mono- or polyamines with phosgene, in a mixer reactor of the rotor-stator type (and optionally additional subsequent reaction apparatuses) which comprises a substantially rotationally symmetric housing, wherein the housing has a substantially rotationally symmetric mixing chamber with separate inlets for at least two substances and an outlet, wherein the inlet for the first substance is provided in the axis of the mixing chamber and the inlet for the at least second substance is constructed in the form of a plurality of openings arranged rotationally symmetrically to the mixing chamber axis. See, for example, EP 291 819 B1 (believed to correspond to U.S. Pat. No. 4,851,571) and EP 291 820 B1 (corresponds to U.S. Pat. No. 4,915,509).

According to the prior art, mixing units in which each inlet which is constructed in the form of openings arranged rotationally symmetrically to the mixing chamber axis is assigned a pin which can be displaced in the axial direction. By displacing the pin axially, the opening can be penetrated by the pin, and thus freed from any deposits present. It is preferably to displace each pin into the inlet opening, either in the event of an increase in pressure in the feed line or periodically. See, for example, EP 830 894 B1 (corresponds to U.S. Pat. No. 5,931,379).

It is likewise known to carry out reactions which start rapidly, such as the reaction of mono- or polyamines with phosgene, in mixing units which comprise a substantially rotationally symmetric housing, wherein the housing has a substantially rotationally symmetric mixing chamber with separate inlets for at least two substances and an outlet, wherein the inlet for the first substance is provided in the axis of the mixing chamber and the inlet for the at least second substance is radial or lateral with respect to the axis of the mixing chamber and the mixing chamber has no moving parts. See, for example, EP 322 647 B1 (corresponds to U.S. Pat. No. 5,117,048) and WO 2002/002217 A1.

It is moreover known to carry out reactions which start rapidly, such as the reaction of mono- or polyamines with phosgene, in mixing units which comprise a substantially rotationally symmetric housing, wherein the housing has a substantially rotationally symmetric mixing chamber with separate inlets for at least two substances and an outlet, wherein at least both inlets are arranged radially to the axis of the mixing chamber. See, for example, DE 10 034 621 A1, U.S. Pat. No. 4,886,368, and DE 42 20 239 C2.

The quality of the mono- or polyisocyanates prepared in such apparatuses depends decisively on the quality and speed of mixing of the at least two flowable substances. In this context, maintaining a uniform mass flow through the mixer reactor plays a decisive role in particular, since backmixing of substances which have already reacted with one another into the substance streams of the unreacted starting substances can thereby be prevented.

A general criterion of the quality of a mixing apparatus is the mixing time which can be achieved with the particular apparatus. The mixing time of a mixing device which is employed for initiating a rapid reaction, such as the preparation of mono- or polyisocyanates by reaction of mono- or polyamines with phosgene dissolved in an organic solvent; is conventionally 0.0001 s to 5 s, preferably 0.0005 s to 4 s, particularly preferably 0.001 s to 3 s (see, for example, DE 10 2005 014846 A1). Mixing time as used herein is to be understood as meaning the time which passes from the start of the mixing operation until 97.5% of the fluid elements of the mixture obtained have reached a specific mixture fraction. This mixture fraction shall not deviate more than 2.5% from the theoretical final value of the mixture obtained when the state of perfect mixture is assumed. The concept of the mixture break is explained e.g. in J. Warnatz, U. Maas, R. W. Dibble: Combustion, Springer Verlag, Berlin Heidelberg N.Y., 2006, 4th edition, p. 136-137.

The quality of the thorough mixing and the completeness of the prevention of backmixing can be seen concretely from several criteria.

By inadequate mixing, caking up to blockages occurs over the course of time within the inlet openings for the at least second substance, so that the introduction of equal material flowing through all openings is disturbed. This impairs the flow properties through the mixer reactor, such that backmixing increasingly occurs.

The size and size distribution of the amine hydrochloride and carbamoyl chloride particles which form during the reaction, the size of which should be in the nanometer to micrometer range, are a further criterion for the quality of the thoroughness of the mixing. The formation of relatively large amounts of these solids is to be prevented, since formation of large and agglomerated amine hydrochloride particles may occur as a result, the phosgenation of which, as described in the literature, is very slow. (see, for example, WO 2004/056756 A1).

The color or the viscosity of the mono- or polyisocyanates obtained is also a further criterion of the quality of the thoroughness of mixing, since if all side reactions are suppressed completely, a colorless and low-viscosity product may be obtained.

The content of free isocyanate groups (NCO value) in the product obtained is a further criterion of the quality of the thoroughness of mixing, since the content remains low if thorough mixing is inadequate, and drops further if backmixing exists. The content of free isocyanate groups can be determined in a simple manner as the so-called NCO value. The NCO value is determined by reaction of the isocyanate with excess dibutylamine to give the corresponding urea and backtitration of the non-consumed amine with hydrochloric acid standard solution. A high NCO value is preferred for industrially suitable mono- and polyisocyanates.

In the known mixing units of the rotor-stator type, mixing is carried out by a procedure in which the first substance metered axially flows outwards due to the centrifugal form of the first rotor disc and is thereby charged with the second substance introduced, and the two substance streams are mixed with one another by the centrifugal forces.

In the preparation of mono- or polyisocyanates by reaction, by means of a mixing unit of the rotor-stator type, of mono- or polyamines with phosgene dissolved in an organic solvent, the phosgene solution is preferably metered axially to the mixing chamber axis and the amine solution is metered through the rotationally symmetrically arranged inlet openings. This originates from the fact that the inlet of the amine solution is more susceptible to blockages and the amine solution is therefore preferably metered through the inlet openings, to each of which is assigned a pin with which the deposits can be removed.

A disadvantage of the known mixer reactors of the rotor-stator type is that two solutions having viscosities of which the ratio is less than 0.5 or greater than 2 can no longer be mixed adequately if the substance having the lower viscosity is metered axially along the mixing chamber axis, since its centrifugal force as it is transferred through the first rotor disc is no longer sufficient to displace the second substance of higher viscosity as it emerges from the rotationally symmetrically arranged openings in the direction of the outlet of the mixing chamber. As a result, backmixing occurs in the mixing chamber, which is, in particular, problematic on the front plate which modifies the cross-section of the housing and on the inside of the housing walls between the stators. This backmixing leads to caking of solids and to a low content of free isocyanate groups in the mono- or polyisocyanates obtained from the mixer reactor.

A disadvantage of the known mixer reactors of the rotor-stator type is moreover that the concentrations of the dissolved substances cannot be chosen as desired. Unfortunately, in the known mixer reactors, the concentration of the solution of higher viscosity is limited by the fact that its viscosity may not be more than twice the viscosity of the at least second solution. This is a disadvantage in particular in the preparation of mono- or polyisocyanates by reaction of mono- or polyamines with phosgene in organic solvents, since the viscosity of the mono- or polyamine solution changes or varies greatly with the concentration of the mono- or polyamine present in the solution, although the viscosity of the phosgene solution increases only slightly at different phosgene concentrations. Thus, the viscosity of solutions of phosgene in monochlorobenzene (MCB) in the concentration range of from 0 to 80 wt. % at 0° C. is between 0.5 and 1.0 mPa·s (viscosity 0.765 mPa·s and density 1.27 g/l at 0° C. and 50 or 56 wt. %), while the viscosity of a solution of methylenediphenyldiamine (MDA) in monochlorobenzene in the concentration range of from 15 to 65 wt. % at 25° C. is between 1 and 200 mPa·s (see Table 1). On the other hand, the difference in density between the solution is only slight and does not have the effect of making the mixing task difficult.

TABLE 1

Density and viscosities of various MDA in MCB solutions at 25° C., determined with a Höppler falling ball viscometer from Haake in accordance with DIN 53015

| Concentration of MDA in MCB (%) | Temperature in ° C. | Density in g/ml | Viscosity in mPa s |
|---|---|---|---|
| 15 | 25 | 1.10 | 0.99 |
| 30 | 25 | 1.10 | 1.89 |
| 45 | 25 | 1.10 | 4.29 |
| 50 | 25 | 1.10 | 5.40 |
| 65 | 25 | 1.14 | 20.98 |
| 95 | 25 | 1.20 | >200 |

Accordingly, it is an object of the present invention to provide a mixer reactor which bypasses the disadvantages mentioned above, and which also ensures a thorough mixing for two flowable substances of widely different viscosities in a quality and speed. In particular, this mixer reactor should allow a process for the preparation of mono- or polyisocyanates with a high content of free isocyanate groups, and therefore makes it possible to use of highly concentrated amine and phosgene solutions.

SUMMARY OF THE INVENTION

The present invention relates to a mixer reactor of the rotor-stator type. This mixer reactor comprising a substantially rotationally symmetric housing which contains a distributing chamber, a mixing chamber, and a front plate having front and rear faces, and a center inlet which transverses from the rear face to the front face, and this front plate modifies the cross-section of the housing between the distributing chamber and the mixing chamber. The rear face of the front plate is closest to the distributing chamber and the front face of the front plate is closest to the mixing chamber. In addition, there are separate inlets into the mixing chamber for at least two different substances, and an outlet from the mixing chamber by which the mixture or product exits the mixing chamber. There is also an inlet in the housing into the distributing chamber for introducing a first substance, which passes into a means for transporting this first substance to the center inlet of the front plate, along the axis of rotation of the mixing chamber. The housing also has a second inlet into the distributing chamber for introducing the second substance into the distributing chamber.

The front plate which modifies the cross-section of the housing between the two chambers, contains a plurality of parallel inlet openings (which transverse from the rear face to the front face of the front plate), with these inlet openings being arranged in a rotationally symmetrically manner around the center inlet. It is through these inlet openings that the second substance is transported from the distributing chamber to the mixing chamber. In addition, the front plate also has a plurality of channels which radiate outwardly from the center inlet of the front plate, and through which the first substance flows from the center inlet of the front plate into the mixing chamber. These channels are preferably symmetrically arranged in an alternating manner with the plurality of parallel inlet openings for the second substance. There is also a plurality of pins which corresponds to the number of parallel inlet openings in the front plate, and these pins can be axially displaced, preferably on an individual basis.

The center inlet of the front plate is preferably located in the axis of rotation such that the first substance flows along the axis of rotation as it enters this center inlet.

DETAILED DESCRIPTION OF THE INVENTION

Figure 1:
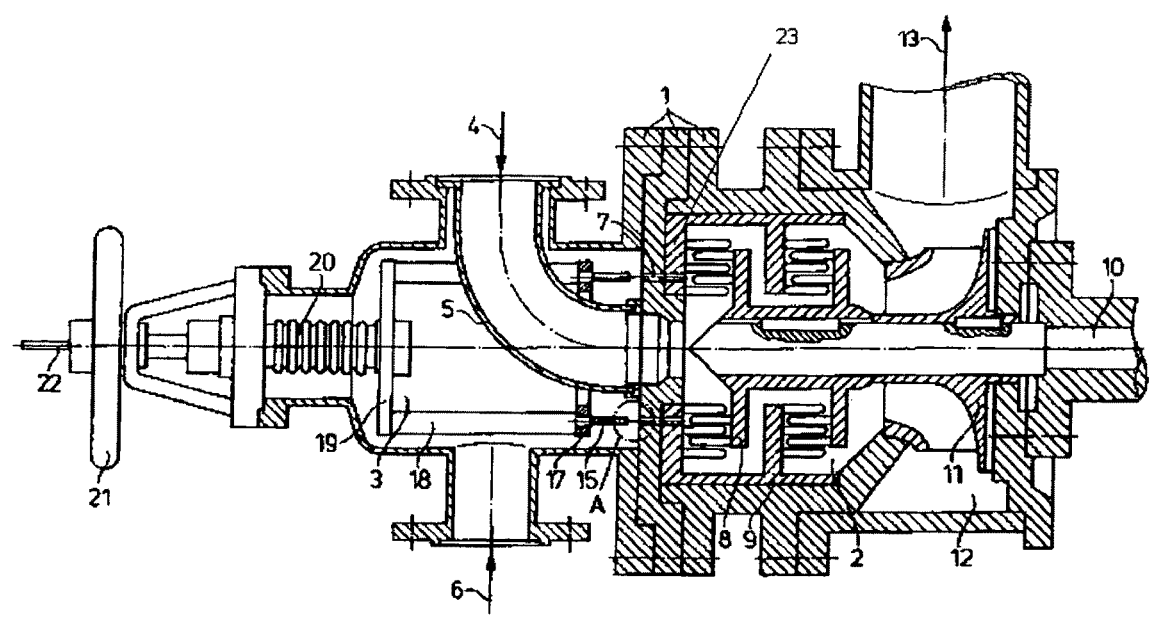
FIG. 1 is a cross-sectional side view of a mixer reactor according to the invention of the rotor-stator type which comprises a front plate with channels.

The mixer reactor according to the invention is suitable for mixing and carrying out or initiating a reaction of at least two, flowable substances. It is preferably employed for the mixing of at least two flowable substances, suspensions or solutions in which the ratio of the viscosities of the first substance and of the at least second substance on entry into the mixer reactor is less than 0.5 or greater than 2, wherein the determination of the viscosity uses a Höppler falling ball viscometer from Haake in accordance with DIN 53015. The mixer reactor is particularly suitable for mixing and carrying out or initiating a phosgenation reaction in which phosgene dissolved in a solvent is employed as the first substance and a solution of a primary amine is employed as the second substance.

On the front face of the front plate, there is a plurality of channels. Preferably, these channels lead radially outwards from the center inlet present in the front plate through which the first substance enters into the mixing chamber along the axis of rotation of the mixing chamber, which runs through this center inlet in the front plate. These channels preferably end at a point which is equidistant from the axis of rotation with the outer most point of the inlet openings for the at least second substance which lie furthest out from the axis of rotation. The channels may be configured as depressions in the front plate or as attached guides and can have a variety of shapes. In other words, the channels may be shaped, for example, in a triangular, a rectangular, a semicircular or an oval cross-section. At a minimum, the channels are open at least at their start, that is to say at the point which is physically closest to the center inlet for the first substance stream, and at least at their end, that is to say at the point or site which is physically farthest away from the center inlet for the first substance stream. As above, in a preferred embodiment, the end of each of these channels is also open at a point or site which is equidistant from the axis of rotation with the outer most point of the inlet openings for the second stream which lies the furthest outward in the radial direction. The region of the channels which lies in between can be either open or closed. By closed, it is meant that these channels are masked by coverings (such as, for example, by plates) which extend in the direction of the mixing chamber, and open only in the flow direction parallel to the plane of the front plate. Thus, the first substance flows through the center inlet, into the channels, and exits from the channels and enters into the mixing chamber.

In a preferred embodiment, the channels are preferably closed or masked in the region lying in between, i.e. at the start or slightly beyond the start of the channels up to a point close to (or slightly before) the end of the channels, because mixing with the second substance inside the mixing chamber then takes place even faster and better. The channels are preferably closed or masked over 5% to 95% of their length, more preferably over 20% to 90% of their length, and most preferably over 40% to 85% of their length. In accordance with the present invention, any combination of these upper and lower ranges, inclusive, may be used. In another preferred embodiment, the coverings already cover the channels at the level of the center inlet for the first substance, such that the first substance must necessarily flow through the channels, and then leaves the channels through the channel openings for the first stream, enters into the mixing chamber, and is mixed in the mixing chamber with the second substance.

Although any number of channels may be used in accordance with the present invention, it is preferred that there are between 2 and 48 channels in or on the front face of the front plate in the direction of the mixing chamber. Furthermore, it is preferred that the mixer reactor has between 2 and 48 openings (i.e. inlet openings) in the front plate through which the second substance stream exits the distributing chamber and enters the mixing chamber. These openings (i.e. inlet openings) for the second substance stream are preferably arranged on one, two or three concentric circles around the axis of rotation. It is also within the scope of the invention, however, that the inlet openings can be arranged on still more concentric circles around the axis of rotation.

The mixer reactor according to the invention is particularly suitable as a phosgenation reactor for the preparation of mono- or polyisocyanates. In this phosgenation reaction, phosgene dissolved in an organic solvent is employed as the first substance, and primary mono- or polyamine optionally dissolved in a solvent is employed as the at least second substance.

The present invention also relates to a process for the preparation of (mono- or poly-) isocyanates by phosgenation of primary amines, in which the primary amines and phosgene are mixed and reacted in the mixer reactor as described herein. In this process using this mixer reactor, it is preferred that the phosgene dissolved in a solvent is employed as the first substance, and a solution of a primary amine is employed as the second substance. The ratio of the viscosities of the first and of the second substance on entry into the mixer reactor is preferably less than 0.5. In this context, the viscosity of these substances is preferably determined using a Höppler falling ball viscometer from Haake in accordance with DIN 53015.

Suitable starting substances and reaction conditions are disclosed in, for example, EP 291 819 B1, EP 322 647.B1 and EP 1616 857 A1 which are believed to correspond to U.S. Pat. Nos. 4,851,571, 5,117,048 and U.S. Published Application 20060025556, respectively, the disclosures of which are herein incorporated by reference.

The mixer reactor according to the invention is suitable for the phosgenation of any desired primary mono- and polyamines, and in particular, for the preparation of the organic polyisocyanates conventionally known and used in field of polyurethane chemistry. This includes organic polyisocyanates such as, for example, the di- and polyisocyanates of the diphenylmethane series (MDI, monomeric MDI and/or polymeric MDI), toluene-diisocyanate (TDI), xylene-diisocyanate (XDI), hexamethylene-diisocyanate (HDI), isophorone-diisocyanate (IPDI) or naphthalene-diisocyanate. Preferred starting materials for the process in accordance with the present invention are the 3 to 95 wt. % strength, and preferably 20 to 75 wt. % strength solutions of phosgene in suitable solvents, and the 5 to 95 wt. % strength, and preferably 20 to 70 wt. % strength solutions of mono- or polyamines in suitable solvents.

Suitable solvents for the preparation of the phosgene and amine solution are any desired solvents which are inert under the reaction conditions. Solvents such as, for example, chlorobenzene, ortho-dichlorobenzene, dioxane, toluene, xylene, methylene chloride, perchloroethylene, trichlorofluoromethane or butyl acetate are suitable.

Chlorobenzene or ortho-dichlorobenzene are preferably employed as solvents. The solvents can be employed in the pure form or as any desired mixtures of the solvents mentioned by way of example. The same solvent or solvent mixture is expediently employed for the amine component and the phosgene, although this is not absolutely necessary.

The phosgene solutions and amine solutions are preferably employed in the mixer reactor in amounts such that a molar ratio of phosgene:primary amino groups of from 1.1:1 to 30:1, and more preferably from 1.25:1 to 3:1 is present in the mixing space of the mixing chamber.

The phosgene solutions and amine solutions employed can be temperature-controlled before introduction into the mixer reactor. The phosgene solution conventionally has a preferred temperature of from −50° C. to +80° C., and more preferably from −20° C. to +70° C. The amine solution can be temperature-controlled at a preferred temperature of from +25° C. to +160° C., and more preferably +40° C. to +140° C. The temperature of the amine solution is controlled so that it is most preferably between +50 and +120° C. The temperature control and metering of the educt solutions is preferably carried out at a pressure level which is above the vapor pressure of the particular solution. The phosgene solutions and amine solutions are most particularly preferably employed at temperatures of from 0° C. to +70° C. and +80° C. to +120° C., respectively. In this context, absolute pressure of from 1 to 70 bar, and preferably 3 to 45 bar can be used.

For mixing of the phosgene solution and the amine solution in the mixer reactor, this can be heated, insulated or cooled, with it preferably being merely insulated. The insulation can be effected by the various methods known in the art and can include the mixing unit.

Figure 2:
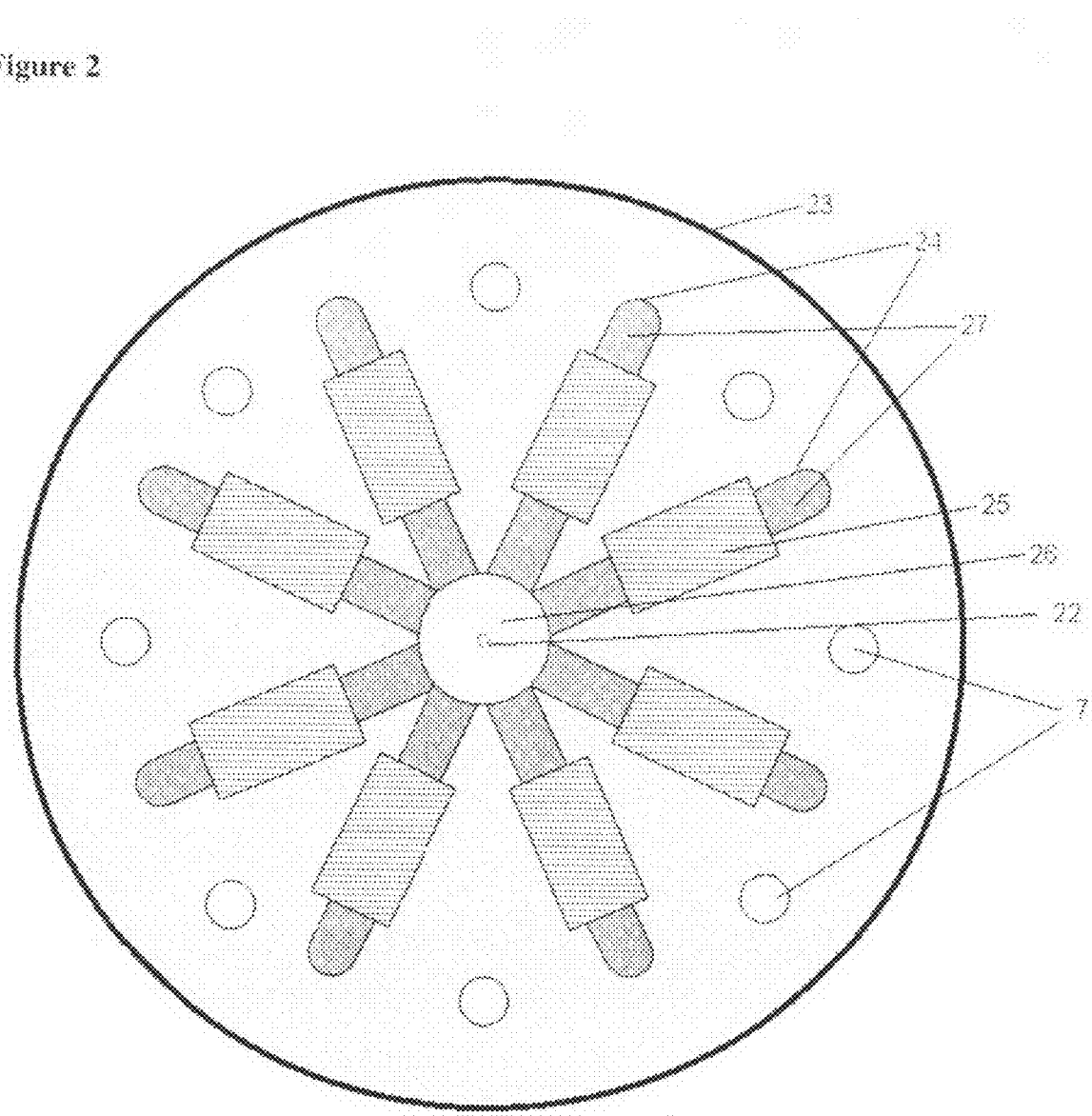
FIG. 2 is a frontal view of the front face of a front plate which is a constituent of the mixer reactor according to the invention.

A more detailed description of the invention will now be provided with the aid of FIGS. 1 and 2.

Reference will now be made to one embodiment of the present invention as illustrated in FIG. 1, a cross-sectional view of the mixer reactor. This mixer reactor comprises a housing 1 which has a mixing chamber 2 and a distributing chamber 3. The at least first substance stream 4 is axially introduced via an inlet, preferably via a curved tube 5, which enters laterally into the outer wall of the distributing chamber wall 3, and transports the first substance stream into the mixing chamber through a center inlet (not shown in FIG. 1) in the front plate 23. This center inlet in the front plate for the first substance is arranged in the axis of rotation 22 (fictional) as it enters into the mixing chamber 2. From this center inlet (not shown in FIG. 1), the first substance is passed via channels (not shown in FIG. 1) in the front plate 23 up to the channel openings 27 for the first substance (not shown in FIG. 1). The second substance stream 6 is introduced into the distributing chamber 3 via an inlet and then enters into the mixing chamber 2 via a plurality of parallel inlet openings 7 which are arranged concentrically in the front plate 23 to the axis of rotation 22 (fictional) of the mixer reactor. The mixing chamber 2 preferably contains rotor elements 8 driven via an axis 10 arranged on the (fictional) axis of rotation 22, and stator elements 9 which are joined to the housing. (As an aside, it is noted that the mixing chamber 2 itself does not actually rotate, but the rotor elements 8 within the mixing chamber 2 are driven by the axis 10.) A running wheel 11 which conveys the mixture via the annular channel 12 into the outlet tube 13 is also preferably present. Each of the inlet openings 7 is assigned a pin 15 which may be axially displaced. The pins 15 are preferably fixed on a carrier ring 17. The carrier ring 17 is joined via a spacer piece 18 to a plate 19 which can be displaced in the axial direction via an axis 10 by means of the hand wheel 21. The passage of this axis 10 through the distributing chamber 3 wall is encapsulated in a gas-tight manner by means of bellows 20.

In accordance with the present invention, axial displacement of the pins 15 pushes each pin 15 through the corresponding inlet opening 7, thus cleans and/or displaces any solids or other residues remaining on, around or in the inlet openings 7.

FIG. 2 shows a front view of a front plate 23 which is a constituent of the mixer reactor according to the invention shown in FIG. 1. The front plate 23 has an center inlet 26 for the first substance stream, and a plurality of channels 24 which pass this first substance on radially out from the center inlet 26 of the front face of the front plate 23 to the same distance as the plurality of parallel inlet openings 7 are from the axis of rotation 22 for the at least second stream. The channels 24 can be installed, for example, either as depressions in or as attachments on the front plate 23. Also, these channels 24 can be opened completely, but are preferably masked completely or partly from the mixing chamber with coverings 25 in the region of from 5 to 95% of their length. The first substance stream is then passed through the center inlet 26 of the front plate 23, flows through the channels 24 which are optionally covered with the coverings 25 and then leaves (or exits) the channels 24 through the channel openings 27 and enters into the mixing chamber 2 (not shown in FIG. 2). In a preferred embodiment (not shown in FIG. 2), the coverings 25 already cover the channels 24 at the level or point of the center inlet 26 for the first substance, so that the first substance stream must necessarily flow through the channels and then leaves the channels through the channel openings 27 and enter into the mixing chamber 2 (not shown in FIG. 2).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A rotor-stator type mixer reactor which comprises a substantially rotationally symmetric housing which comprises
    a) a distributing chamber,
    b) a mixing chamber,
    c) a front plate having a rear face, a front face, and a center inlet which transverses from the rear face to the front face, wherein said front plate modifies the cross-section of said housing between said distributing chamber and said mixing chamber, with the rear face of said front plate being closest to said distributing chamber and the front face of said front plate being closest to said mixing chamber,
    d) an inlet in the housing near the distributing chamber for introducing a $1^{st}$ substance,
    e) a means for transporting said $1^{st}$ substance from said inlet d) to the center inlet of said front plate,
    f) a second inlet in the housing for introducing a $2^{nd}$ substance into said distributing chamber,
    g) a plurality of parallel inlet openings in said front plate which are arranged in a rotationally symmetrically manner in said front plate and through which the $2^{nd}$ substance is transported from said distributing chamber to said mixing chamber,
    h) a plurality of channels which radiate outwardly from the center inlet of said front plate and through which the $1^{st}$ substance is transported from said transporting means into said mixing chamber, wherein said channels are arranged in, on, or above the front face of said front plate, i) a plurality of pins which correspond to the plurality of parallel inlet openings in said front plate, and said pins can be axially displaced, and j) an outlet in the mixing chamber through which the mixed material is removed.

2. The mixer reactor of claim 1, wherein said plurality of channels present in the front plate extend outwardly from the center inlet for the $1^{st}$ substance in the radial direction up to the site at which the plurality of parallel inlet openings are present in said front plate which lie furthest out are arranged, such that the ends of said channels are equidistant from the center of said center inlet with the outermost point of each of said parallel inlet openings.

3. The mixer reactor of claim 1, wherein said plurality of channels are partially closed in the direction of said mixing chamber by a covering on each channel, such that the channels are closed 5 to 95% of their length.

4. The mixer reactor of claim 1, wherein mixing chamber additionally comprises rotor elements and stator elements on an axis of rotation through the center of said mixing chamber.

5. The mixer reactor of claim 1, wherein said plurality of pins are fixed to a carrier ring which is joined via a spacer piece to a plate in the distributing chamber.

6. The mixer reactor of claim 5, wherein said plate is displaced in the axial direction by an axis which is connected to a hand wheel which is located outside of the distributing chamber, in which said axis is encapsulated in a gas-tight manner as it passes through the distributing chamber by means of a bellows.

7. The mixer reactor of claim 1, wherein said means for transporting said $1^{st}$ substance from said inlet d) to the center of said front plate is a curved tube.

8. The mixer reactor of claim 1, wherein said mixing chamber additionally comprises a running wheel which conveys the mixture via an annular channel into said outlet tube.

9. The mixer reactor of claim 3, wherein the channels are closed over 20 to 90% of their length.

10. The mixer reactor of claim 1, in which the number of channels for the $1^{st}$ substance ranges from 2 to 48 and the number of inlet openings for the $2^{nd}$ substance ranges from 2 to 48, wherein the number of channels and the number of inlet openings may be the same or different.

11. The mixer reactor of claim 1 wherein the parallel inlet openings for the $2^{nd}$ substance are arranged on one, two or three concentric circles around the center inlet in said front plate.

12. A process for mixing at least two different substances comprising mixing a first substance and a second substance in the mixer reactor of claim 1, wherein said first substance and said second substance are each individually selected from flowable substances, suspensions or solutions.

13. A process for mixing at least two different substances comprising mixing a first substance and a second substance in the mixer reactor of claim 1, wherein the ratio of the viscosities of said first substance and said second substance on entry into said mixer reactor is less than 0.5 or greater than 2.

14. The process of claim 12, wherein said first substance comprises phosgene dissolved in a solvent, and said second substance comprises a solution of a primary amine.

15. In a process for the preparation of isocyanates comprising phosgenation of primary amines, the improvement wherein the primary amines and phosgene are mixed and reacted in the mixer reactor of claim 1.

16. The process of claim 15, wherein phosgene dissolved in a solvent is employed as said first substance and a solution of a primary amine is employed as said second substance, with the ratio of the viscosities of said first and of second substances on entry into the mixer reactor being less than 0.5.

* * * * *